(12) United States Patent
Pacetti

(10) Patent No.: US 8,192,785 B2
(45) Date of Patent: Jun. 5, 2012

(54) APPARATUS AND METHOD FOR COATING IMPLANTABLE DEVICES

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1067 days.

(21) Appl. No.: 11/649,497

(22) Filed: Jan. 3, 2007

(65) Prior Publication Data

US 2007/0110891 A1    May 17, 2007

Related U.S. Application Data

(62) Division of application No. 09/997,390, filed on Nov. 30, 2001, now Pat. No. 7,175,874.

(51) Int. Cl.
*A61L 33/00* (2006.01)

(52) U.S. Cl. ........ 427/2.1; 427/2.3; 427/2.25; 427/2.28; 427/407.1; 528/45; 106/499

(58) Field of Classification Search .............. 427/2.3, 427/137, 136
See application file for complete search history.

(56) References Cited

U.S. PATENT DOCUMENTS

| | | | |
|---|---|---|---|
| 2,072,303 A | 3/1937 | Herrmann et al. | |
| 4,748,043 A | 5/1988 | Seaver et al. | |
| 4,977,901 A | 12/1990 | Ofstead | |
| 5,219,120 A | 6/1993 | Ehrenberg et al. | |
| 5,328,471 A | 7/1994 | Slepian | |
| 5,464,650 A * | 11/1995 | Berg et al. ................. | 427/2.3 |
| 5,578,073 A | 11/1996 | Haimovich et al. | |
| 5,605,696 A | 2/1997 | Eury et al. | |
| 5,624,411 A | 4/1997 | Tuch | |
| 5,628,730 A | 5/1997 | Shapland et al. | |
| 5,667,767 A | 9/1997 | Greff et al. | |
| 5,670,558 A | 9/1997 | Onishi et al. | |
| 5,700,286 A | 12/1997 | Tartaglia et al. | |
| 5,716,981 A | 2/1998 | Hunter et al. | |
| 5,741,554 A | 4/1998 | Tisone | |
| 5,800,392 A | 9/1998 | Racchini | |
| 5,824,049 A | 10/1998 | Ragheb et al. | |
| 5,830,178 A | 11/1998 | Jones et al. | |
| 5,837,313 A | 11/1998 | Ding et al. | |
| 5,851,508 A | 12/1998 | Greff et al. | |
| 5,865,814 A | 2/1999 | Tuch | |
| 5,873,904 A | 2/1999 | Ragheb et al. | |
| 5,971,954 A | 10/1999 | Conway et al. | |
| 5,980,928 A | 11/1999 | Terry | |

(Continued)

FOREIGN PATENT DOCUMENTS

EP       0 665 023       8/1995

(Continued)

OTHER PUBLICATIONS

Barath et al., *Low Dose of Antitumor Agents Prevents Smooth Muscle Cell Proliferation After Endothelial Injury*; JACC vol. 13, No. 2, Feb. 1989:252A (Abstract).

(Continued)

*Primary Examiner* — Dah-Wei Yuan
*Assistant Examiner* — Andrew Bowman
(74) *Attorney, Agent, or Firm* — Squire Sanders (US) LLP

(57) ABSTRACT

A coating for implantable devices, such as stents, and a method of making the same is disclosed. Moreover, an apparatus for depositing the coating is disclosed.

5 Claims, 5 Drawing Sheets

U.S. PATENT DOCUMENTS

| | | | |
|---|---|---|---|
| 5,980,972 | A | 11/1999 | Ding |
| 5,984,449 | A | 11/1999 | Tajika et al. |
| 6,010,530 | A | 1/2000 | Goicoechea |
| 6,015,541 | A | 1/2000 | Greff et al. |
| 6,030,371 | A | 2/2000 | Pursley |
| 6,045,056 | A | 4/2000 | Tardoni |
| 6,056,993 | A | 5/2000 | Leidner et al. |
| 6,093,557 | A | 7/2000 | Pui et al. |
| 6,096,070 | A | 8/2000 | Ragheb et al. |
| 6,140,431 | A | 10/2000 | Kinker et al. |
| 6,153,252 | A | 11/2000 | Hossainy et al. |
| 6,165,212 | A | 12/2000 | Dereume et al. |
| 6,194,034 | B1 | 2/2001 | Nishi et al. |
| 6,368,658 | B1 | 4/2002 | Schwarz et al. |
| 6,572,651 | B1 | 6/2003 | De Scheerder et al. |
| 6,645,552 | B1 * | 11/2003 | Schall et al. ............ 427/137 |
| 6,739,518 | B1 | 5/2004 | Davis et al. |
| 2003/0059520 | A1 | 3/2003 | Chen et al. |

FOREIGN PATENT DOCUMENTS

| | | |
|---|---|---|
| EP | 0 970 711 | 1/2000 |
| WO | WO 91/12846 | 9/1991 |
| WO | WO 97/45105 | 12/1997 |
| WO | WO 99/63981 | 12/1999 |
| WO | WO 00/12147 | 3/2000 |
| WO | WO 00/64506 | 11/2000 |
| WO | WO 01/45763 | 6/2001 |

OTHER PUBLICATIONS

Matsumaru et al., *Embolic Materials for Endovascular Treatment of Cerebral Lesions*; J. Biomater. Sci. Polymer Edn, vol. 8, No. 7 (1997), pp. 555-569.

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6)(1985), pp. 2490-2498.

Miyazawa et al., *Effects of Pemirolast and Tranilast on Intimal Thickening After Arterial Injury in the Rat*; J. Cardiovasc. Pharmacol. (1997), pp. 157-162.

Ohsawa et al., *Preventive Effects of an Antiallergic Drug, Pemirolast Potassium, on Restenosis After Percutaneous Transluminal Coronary Angioplasty*; American Heart Journal (Dec. 1998), pp. 1081-1087.

Shigeno, *Prevention of Cerebrovascular Spasm by Bosentan, Novel Endothelin Receptor*; Chemical Abstract 125:212307 (1996).

Perron "The Design and Application of a Reliable Ultrasonic Atomizer", IEEE Transactions on Sonics and Ultrasonics, vol. SU-14, No. 4, pp. 149-153 (1967).

\* cited by examiner

APPARATUS AND METHOD FOR COATING IMPLANTABLE DEVICES

CROSS REFERENCE TO RELATED APPLICATION

This is a divisional application of U.S. Ser. No. 09/997,390, which was filed on Nov. 30, 2001 now U.S. Pat. No. 7,175,874.

BACKGROUND OF THE INVENTION

1. Field of the Invention

This invention relates generally to implantable devices, such as stents. More particularly, the present invention relates to an apparatus and method for coating stents.

2. Description of the Background

Implanting a stent, after a percutaneous transluminal coronary angioplasty (PTCA) procedure, is often used to avoid or mitigate the effects of restenosis at a surgical site. In general, stents are small, cylindrical devices whose structure serves to create or maintain an unobstructed opening within a lumen. Stents are typically made of, for example, stainless steel, Nitinol or other materials and are delivered to the target site via a balloon catheter. Although the stents are effective in opening the stenotic lumen, the foreign material and structure of the stents themselves may exacerbate the occurrence of restenosis or thrombosis.

In addition to using a stent, drugs or therapeutic agents that limit migration and/or proliferation of vascular smooth muscle cells are used to significantly reduce the incidence of restenosis and thrombosis. Examples of therapeutic agents commonly used include heparin, aspirin, IIb/IIa inhibitors, antithrombogenic agents, dexamethasone, steroids, antiinflammatory agents, cytostatic agents, cytotoxic agents, antimicrobials, thrombolytics, monoclonal antibodies, tranilast, and antifibrosis agents. Since the therapeutic agents are applied systemically to the patient, they are absorbed not only by the tissues at the target site, but by other areas of the body. As such, one drawback associated with the systemic application of drugs is that areas of the body not needing treatment are also affected. To provide more site-specific treatment, stents are frequently used as a means of delivering drugs exclusively to the target site. Drugs are suspended in tissue-compatible polymers such as silicones, polyurethanes, polyvinyl alcohol, poly(ethylene-co-vinyl alcohol), polyethylene, hydrogels, substituted methacrylates, poly(ethylene-co-vinyl acetate), and hyaluronic acid and blended mixtures thereof. By positioning the stent at the target site, the drugs can be applied directly to the area of the lumen requiring therapy.

Although stents with a drug coating have been an advance for the treatment of restenosis and other similar vascular ailments, the stents, and the methods and apparatus for their production have not yet been perfected. For instance, conventional techniques often apply a single coating of a homogenous composition that contains a mixture of a polymer and a therapeutic substance. The use of a homogenous composition may have several flaws. The polymeric portion of the coating may not be stable in the vascular environment (i.e., the polymer may leach into the blood), and may not be capable of holding a sufficient amount of the drug. In addition, conventional coatings may not have a blood compatible surface to the vascular environment. Moreover, the drug release rate of a coating made from a homogenous composition cannot be tailored to provide for different release profiles.

As an alternative to using a homogenous composition to coat a stent, some conventional techniques apply a coating to a stent that has more than one layer, with each layer having a different composition. These techniques also suffer from some flaws. For example, the different layers may not strongly adhere to each, thereby allowing one or more layer to leach into the blood or become detached creating an embolization hazard. Also, the coating process of these techniques may not be very efficient because each layer must be applied, and then dried before the next layer is applied. Finally, the application of the composition for each additional layer subsequent to the drying of the previously applied layer can cause the extraction of the drug out of the previous layer. Accordingly, the concentration of the drug will reside in the upper most layers, causing a rapid release of the drug subsequent to the implantation procedure. This "burst-effect" leads to a reduced residence time of the drug at the implantation site, which may be undesirable depending on the type of condition being treated.

Accordingly, what is needed is an apparatus and process for coating stents that does not suffer from the aforementioned drawbacks. More particularly, there is a need for a method and apparatus for coating a stent that is able to modify the coating formulation as the formulation is being applied to the stent.

SUMMARY OF THE INVENTION

The present invention is directed to a method of forming a coating on an implantable device such as a stent including applying a coating formulation to a stent, the coating formulation including a first ingredient and a second ingredient, and modifying the ratio of the first ingredient with respect to the second ingredient in the coating formulation as the coating formulation is being applied to the stent. In one embodiment, the act of applying includes spraying the coating formulation on the stent.

The present invention is further directed to a system for applying a coating on a stent, including a nozzle for spraying a composition onto a stent, a first reservoir in fluid communication with the nozzle for supplying a first ingredient of the composition to the nozzle, a second reservoir in fluid communication with the nozzle for supplying a second ingredient of the composition to the nozzle, and a control assembly for adjusting the amount of the first or second ingredient that is fed into the nozzle wherein the amount of the first or second ingredient that is sprayed by the nozzle can be modified by the control assembly without interrupting the application of the composition onto the stent. The system may further have a mixer for mixing the first ingredient with the second ingredient. In one embodiment, the control assembly includes a valve for adjusting the input rate of the first or second ingredient to the nozzle.

The present invention is also directed to an implantable medical device having a coating having a first ingredient and a second ingredient, wherein from a deep region of the coating to a more shallow region of the coating, the ratio of the concentration of the first ingredient to the concentration of the second ingredient gradually increases or decreases.

In the embodiments of the present invention, the ingredients can be a polymeric material and a therapeutic substance. Some examples of polymeric materials can include ethylene vinyl alcohol copolymer, polybutylmethacrylate, polyethylene glycol, amorphous Teflon, and poly(ethylene-co-vinyl acetate). Some examples of therapeutic substances can include actinomycin D, paclitaxel, docetaxel, rapamycin, β-estradiol and BAK Heparin.

DETAILED DESCRIPTION OF THE EMBODIMENTS

System for Coating

Figure 1:
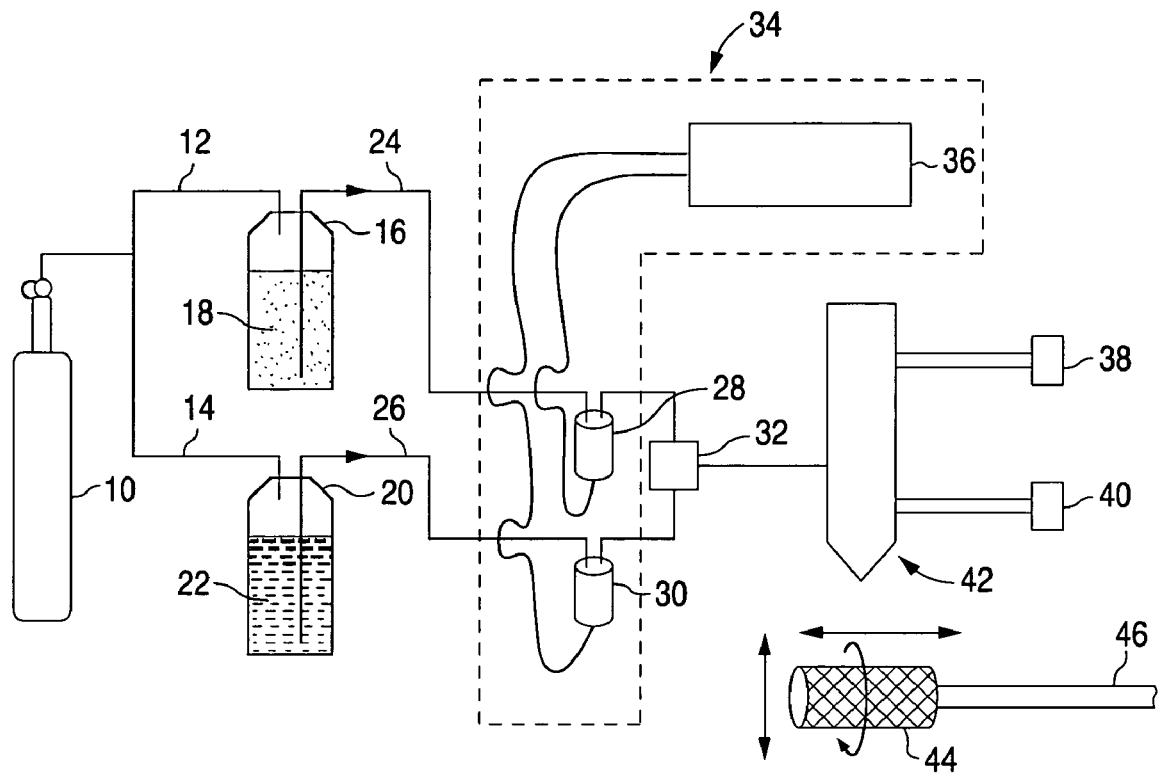
FIG. 1 illustrates a coating system for forming a coating on a stent.

An embodiment of the present invention involving a system for spray coating an implatable device such as a stent is depicted in FIG. 1. Although a spray system is depicted in the spirit of convenience and brevity, it should be noted that other systems and methods are also within the scope of the claimed invention.

Referring to FIG. 1, a gas source such as an air compressor 10 may provide air pressure to a first reservoir 16 and a second reservoir 20 through a first air hose 12 and a second air hose 14, respectively. First reservoir 16 can hold a first solution 18 which includes a first ingredient (e.g., a polymeric material) and a solvent. Second reservoir 20 can hold a second solution 22 which includes a second ingredient (e.g., a therapeutic substance) and a solvent. It is understood that any number of reservoirs can be used to contain any number of ingredients. The air pressure delivered from air compressor 10 can be sufficiently high enough to promote uptake of the solutions in first reservoir 16 and second reservoir 20 into a first fluid hose 24 and a second fluid hose 26. First solution 18 and second solution 22, in turn, can be fed into a control assembly 34, which controls the rate that compositions from first reservoir 16 and second reservoir 20 are delivered to a mixer 32.

First solution 18 and second solution 22 are mixed in mixer 32, and then moved as a mixed solution to a nozzle 42. As the mixed solution enters the chamber of nozzle 42, the mixed solution is exposed to pressurized air from two sources: an actuating gas source 38 and an atomizing gas source 40. Atomizing gas source 40, which can deliver air or another gas, provides sufficient pressure and velocity to atomize the solution into small droplets. Actuating gas source 38, on the other hand, can provide a sufficient amount of pressure so that the droplets are forced out of nozzle 42 and directed to a target (e.g., a stent).

As noted above, control assembly 34 can monitor and control the rate of fluid delivered to mixer 32 and nozzle 42. Control assembly 34 can have a controller 36 (e.g., a CPU) that is in communication with a first valve 28 and a second valve 30. First valve 28 and second valve 30 may be, for example, high precision proportioning valves as is well known and commonly available to those of ordinary skill in the art. Alternatively, first valve 28 and second valve 30 could be very low volume, high speed valves (Lee Electro-Fluidic Systems, Westbrook, Conn.).

Figure 2:
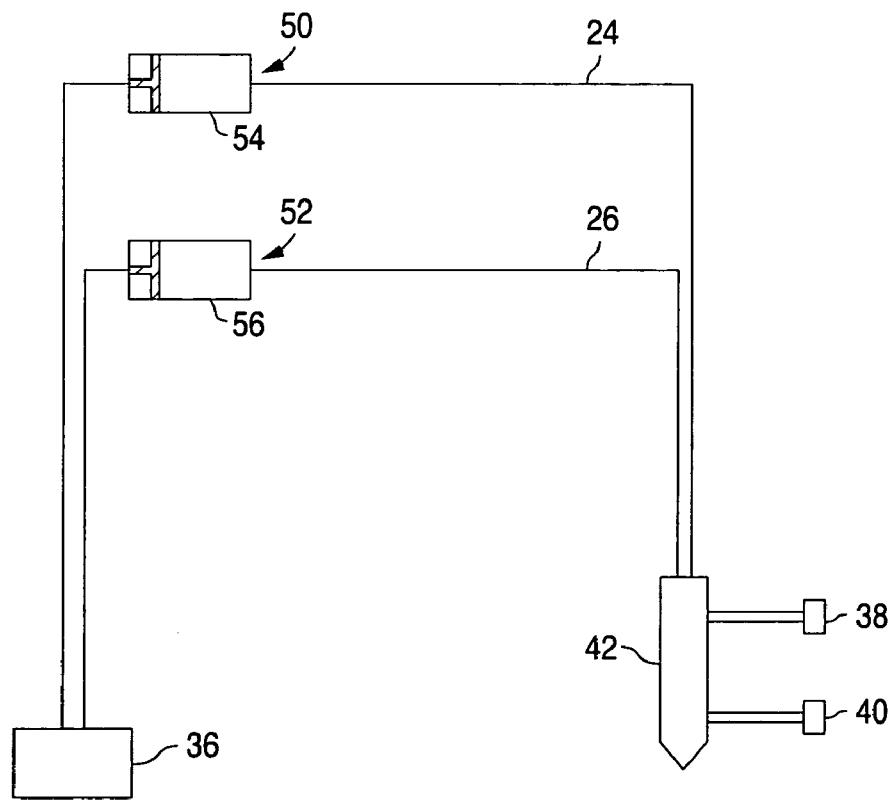
FIG. 2 illustrates a coating system for forming a coating on a stent.

In another embodiment, referring to FIG. 2, a first reservoir 54 and a second reservoir 56 are in fluid communication with nozzle 42 for delivering two different ingredients to nozzle 42. Instead of a gas source such as air compressor 10, a first syringe pump 50 and a second syringe pump 52 may provide pressure to first reservoir 54 and second reservoir 56, respectively. Syringe pumps 50 and 52, in turn, are in communication with controller 36. Controller 36 may provide signals to syringe pumps 50 and 52 and control the amount of motive force that syringe pumps 50 and 52 provide to reservoirs 54 and 56, thereby controlling the amount of ingredients that are ultimately delivered to nozzle 42.

Various approaches may be used to mix the ingredients delivered by the reservoirs. In one embodiment, referring to FIG. 1, the ingredients are mixed in mixer 32 before they are delivered to nozzle 42. Representative examples of types of mixers that can be employed include an ultrasonic mixer having a piezoelectric transducer, a static mixer and a mechanical mixer. Alternatively, the ingredients can be mixed as the ingredients are introduced into and/or ejected out from nozzle 42.

Various structures can be used to support the stents while they are being sprayed by nozzle 42. By way of example, and not limitation, a stent 44 (FIG. 1) can be attached to a mandrel 46 that rotates and/or moves in a linear direction during the application process. Alternatively, nozzle 42 can pivotly rotate around and move linearly along a stationary stent.

Method of Applying Coating

In one embodiment of the present invention, a method is used to apply a coating formulation to a stent, whereby the coating formulation has at least two ingredients and the relative concentrations of the ingredients are modified as the coating formulation is applied to the stent. In one embodiment, the coating formulation is applied to the stent by spraying. Referring to FIG. 1, first solution 18 can contain a first ingredient (e.g., a polymeric material), and second solution 22 can contain a second ingredient (e.g., a therapeutic substance). A gas source such as air compressor 10 can provide the motive force to deliver first solution 18 and second solution 22 to first valve 28 and second valve 30, respectively. Control assembly 34 can be used to control the amount of first solution 18 and second solution 22 that is delivered to mixer 32, and ultimately the amount delivered to nozzle 42. For example, while nozzle 42 is spraying a stent, controller 36 can modify the ratio of first solution 18 with respect to second solution 22 by controlling the operation of first and second valve 28 and 30.

Figure 3:
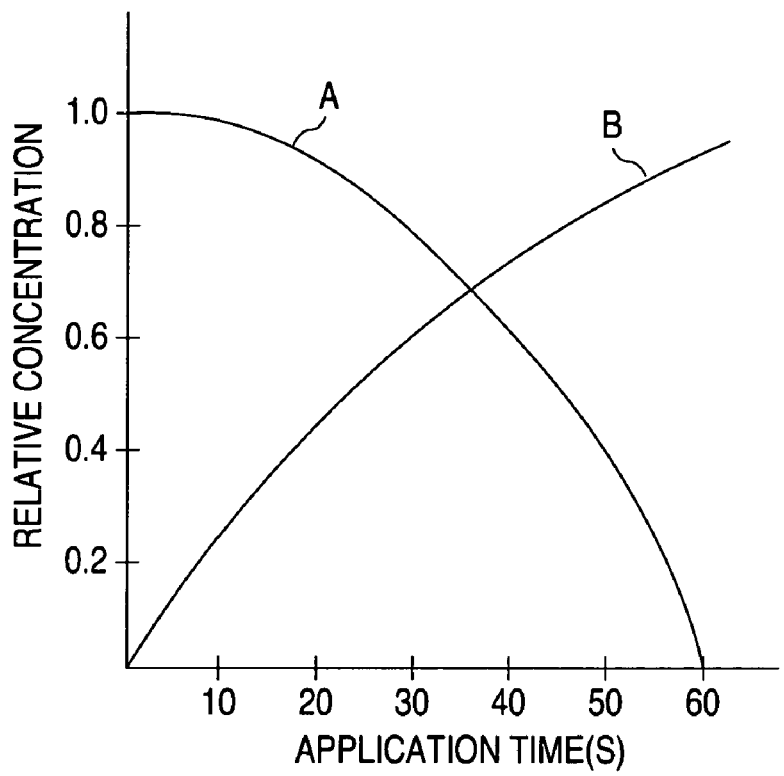
FIG. 3 is a graph showing the relative concentration of two ingredients as a function of application time.

In one embodiment, for example, first solution 18 contains ingredient A (a therapeutic substance), and second solution 22 contains ingredient B (a polymeric material). While nozzle 42 is spraying stent 44, controller 36 can send signals to first valve 28 to reduce the flow rate of first solution 18. As a result, the amount of first solution 18, and therefore ingredient A, that is delivered to mixer 32 is reduced, thereby modifying the contents of the composition of the coating formation that is sprayed onto stent 44. In addition, while nozzle 42 is spraying stent 44, controller 36 can send signals to second valve 30 to increase the flow rate of second solution 22. For example, as shown in FIG. 3, at the early segments of the application process, the concentration of ingredient A relative to the concentration of ingredient B is significantly higher. However, as the application process proceeds, the concentration of ingredient B can be incrementally increased while the concentration of ingredient A is concurrently decreased relative to the concentration of ingredient B.

Figure 4:
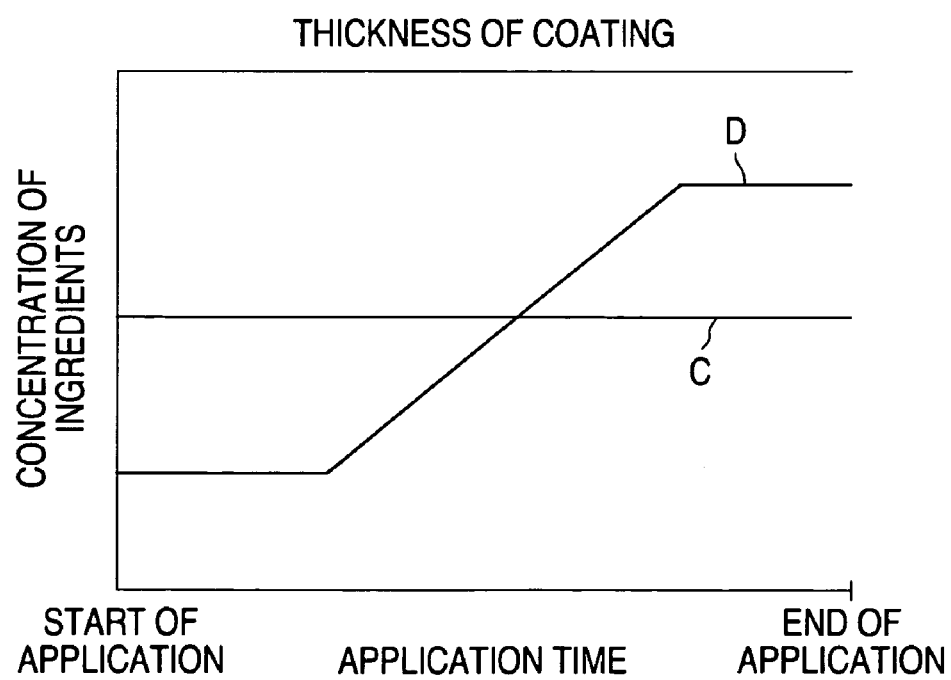
FIGS. 4 and 5 are graphs, in accordance with two embodiments, showing the concentration of two ingredients as a function of application time and thickness of the coating.

In another embodiment, the coating formulation contains ingredient C and ingredient D. Referring to FIG. 4, the concentration of ingredient C can remain constant as the coating is applied, while the concentration of ingredient D remains constant for an initial period, then increases, and then becomes constant at a later stage of the application.

Figure 5:
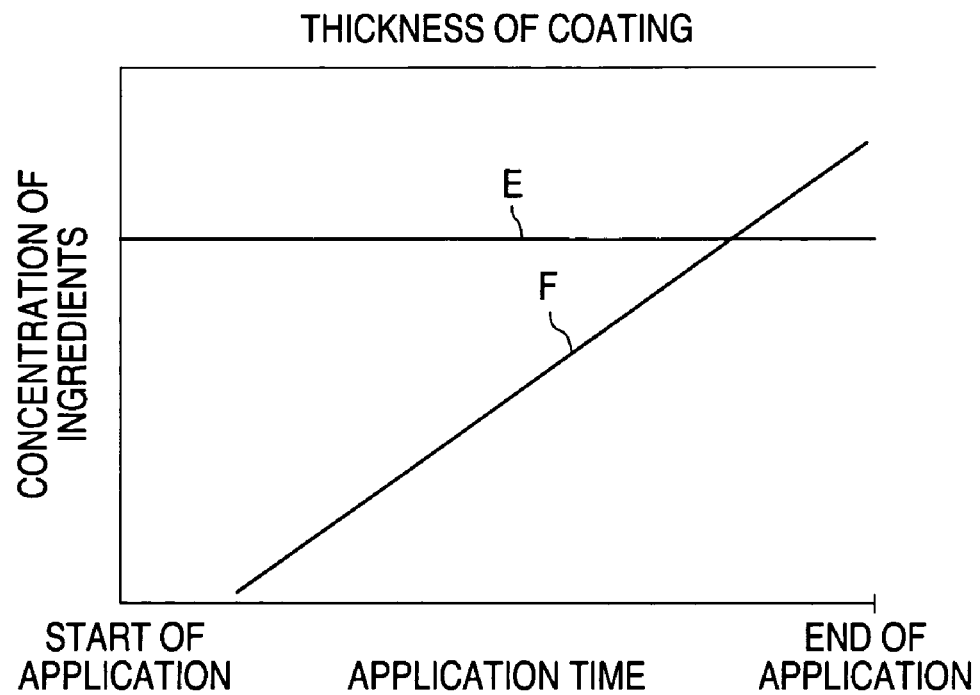

In a yet another embodiment, the coating formulation can contain ingredient E and ingredient F. Referring to FIG. 5, ingredient E can first be applied as a primer, and then ingredient F can be gradually mixed with ingredient E at an increasing concentration.

In one exemplary implementation of the ingredients of FIG. 5, ingredient E can be ethylene vinyl alcohol copolymer (EVAL), and ingredient F can be polyethylene glycol (PEG). EVAL is considered to have relatively good adhesion potential, whereas PEG is considered to have relatively high blood compatibility. A single coating with a large fraction of PEG relative to EVAL would likely give high blood compatibility but would swell significantly, perhaps dissolving off of the stent, releasing PEG into the blood, and generally not adhering well to the stent. A formulation with a high percentage of EVAL, in turn, would likely adhere to the stent surface, but would not be as blood compatible as PEG. In order to realize the benefits of combining EVAL and PEG, one could apply a coating formulation as shown in FIG. 5.

Figure 6:
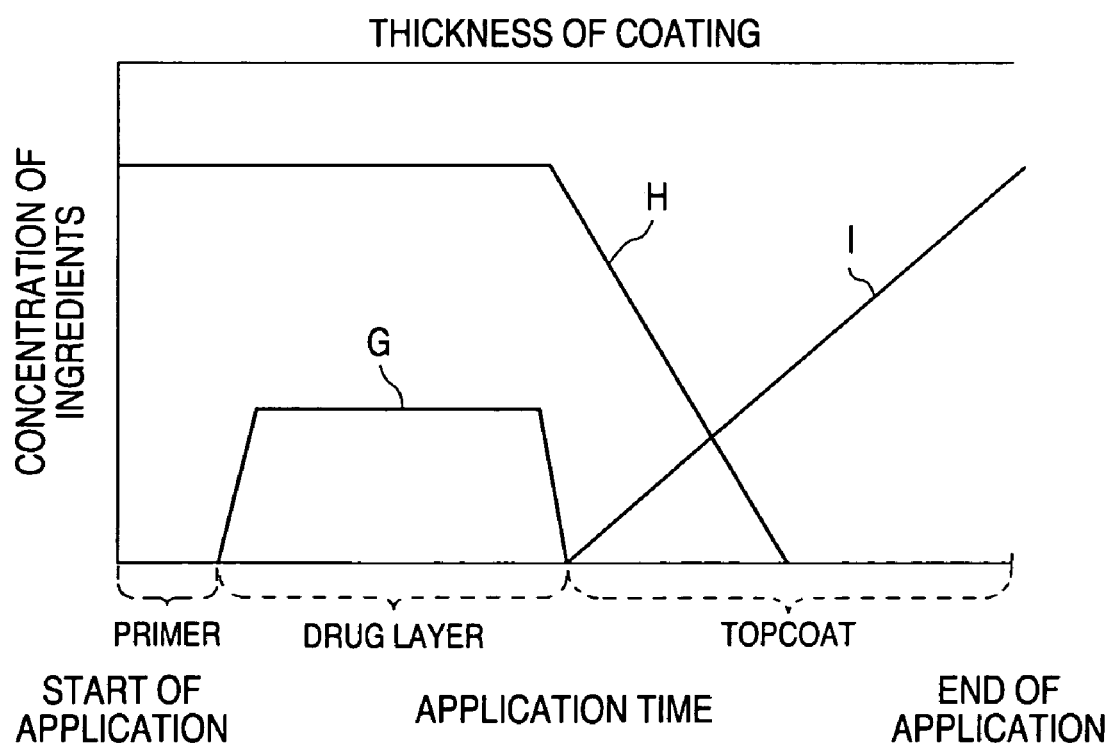
FIGS. 6 and 7 are graphs, in accordance with other embodiments, showing the concentration of three ingredients as a function of application time and thickness of the coating.

In another embodiment, the coating formulation contains ingredient G, ingredient H and ingredient I. By way of example and not limitation, ingredient G can be a therapeutic substance, ingredient H can be EVAL, and ingredient I can be poly(ethylene-co-vinyl acetate). Referring to FIG. 6, ingredient H can be first applied to the stent at constant concentration as a primer. Then, ingredient G can be added with an increasing concentration to provide a drug layer. About one-half the way through the application process, ingredient I is added to the coating formulation. The concentration of ingredient I increases through the rest of the coating process, while the concentration of ingredient H decreases. At the end of the coating process, with respect to ingredient G, ingredient H and ingredient I, the coating formulation only contains ingredient I, thereby providing a topcoat layer.

Figure 7:
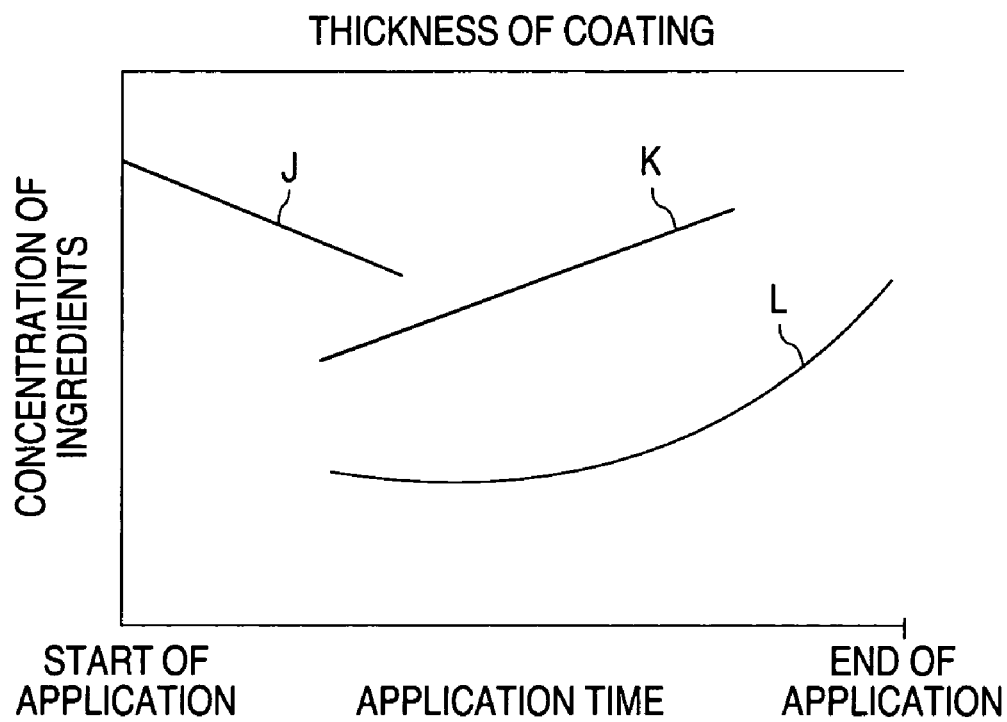

In another embodiment, the coating formulation contains ingredient J, ingredient K and ingredient L. Referring to FIG. 7, ingredient J is initially applied to a stent as a primer. However, as the application process continues, the concentration of ingredient J in the coating formulation decreases. While ingredient J is being applied, ingredients K and L are added to the coating formulation, and the concentrations of ingredient K and L increase throughout the remainder of the coating application. For example, ingredient J is polybutylmethylmethacrylate (PBMA), ingredient K is EVAL and ingredient L is Actinomycin D, with the common solvent dimethylacetamide.

Implantable Device

A stent is broadly intended to include self-expandable stents, balloon-expandable stents, and stent-grafts. One of ordinary skill in the art, however, understands that other medical devices on which a polymeric material can be coated can be used with the practice of the present invention, such as grafts (e.g., aortic grafts), artificial heart valves, cerebrospinal fluid shunts, axius coronary shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (e.g., ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

Figure 8:
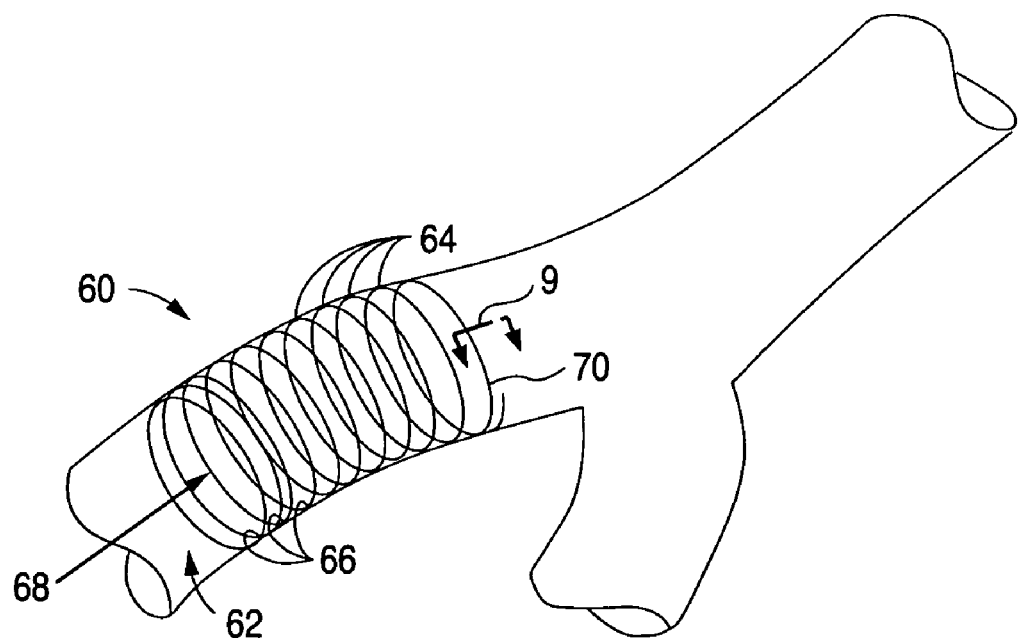
FIG. 8 is a diagram of an embodiment of an implantable medical device inserted into a body vessel.

FIG. 8 illustrates an implantable prosthetic medical device. In the spirit of convenience and brevity, the medical device referenced in the text and figures of the present disclosure is a stent 60. Stent 60 can be cylindrical or tubular in shape, and can be inserted into a body lumen 62. The structure of stent 60 should allow stent 60 to be inserted into and physically uphold an anatomical passageway such as body lumen 62, by exerting a radially outward-extending force against the walls or inner lumen surface of the passageway. If desired, stent 60 can also expand the opening of lumen 62 to a diameter greater than its original diameter and, thereby, increase fluid flow through lumen 62.

Stent 60 can include struts 70 that form a network structure. Struts 70 have an outer (or lumen contacting) surface 64 and an inner surface 66, as shown in FIG. 8. In addition, a hollow bore 68 extends longitudinally through the body structure of stent 60.

Figure 9:
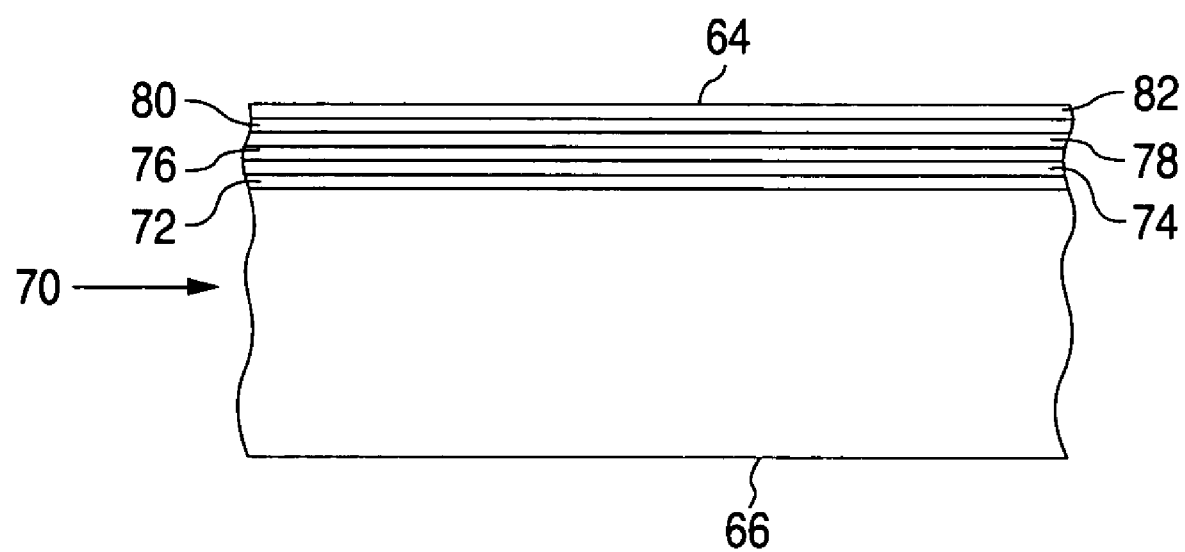
FIG. 9 illustrates a partial cross-section of a strut, in accordance with one exemplary embodiment, along the line 9-9 of FIG. 8.

In one embodiment of the present invention, a coating formulation with a first ingredient and a second ingredient is used to coat outer surface 64 of struts 70, and the resultant coating has a first region and a second region, where the quantity of the first ingredient with respect to the second ingredient is different in the first region as compared to the second region. In another embodiment, the coating formulation has three or more different ingredients. In a further embodiment, the coating has three or more different regions. Referring to FIG. 9, by way of illustration, the coating of strut 70 has a first region 72, a second region 74, a third region 76, a fourth region 78, a fifth region 80 and a sixth region 82. In the interests of brevity and simplification, the different regions are illustrated only on outer surface 64 of strut 70. However, one of ordinary skill in the art will understand that the coating can also be on inner surface 66 of strut 70, as well as all other surfaces of stent 60.

Referring to FIG. 9, first region 72 may be used as a primer, and fifth region 80 may used as a rate reduction membrane to reduce the release rate of a therapeutic substance contained in second region 74, third region 76, and fourth region 78. Sixth region 82 may be used as a blood compatible layer. Furthermore, by gradually changing the concentration of the ingredients contained in the regions, there may be increased interlayer adhesion. For instance, second region 74, third region 76, fourth region 78, and fifth region 80 can be used for increased interlayer adhesion between first region 72 and sixth region 82. One of ordinary skill in the art will understand that fewer than six regions or more than six regions may be applied as part of the present invention.

By way of example, the coating formulation may include ingredient M, ingredient N, ingredient O and ingredient P. Referring to Table I, for instance, the concentrations of the various ingredients relative to each other may be changed in the different regions.

TABLE I

Concentration Relative to Other Ingredients (%)

| Region | Ingredient M | Ingredient N | Ingredient O | Ingredient P |
|---|---|---|---|---|
| First Region 72 | 100 | 0 | 0 | 0 |
| Second Region 74 | 60 | 20 | 20 | 0 |
| Third Region 76 | 30 | 30 | 30 | 10 |
| Fourth Region 78 | 10 | 40 | 30 | 20 |
| Fifth Region 80 | 0 | 50 | 25 | 25 |
| Sixth Region 82 | 0 | 40 | 20 | 40 |

In yet another embodiment of the present invention, the coating formulation includes ingredient Q, ingredient R, ingredient S and ingredient T. Referring to Table II, for example, the concentrations of the various ingredients may be changed in the different regions. In one exemplary implementation of the ingredients of Table II, ingredient Q is PBMA, ingredient R is EVAL, ingredient S is Actinomycin D, and ingredient T is PEG (molecular weight 15,000 amu).

TABLE II

Concentration (mg/ml)

| Region | Ingredient Q | Ingredient R | Ingredient S | Ingredient T |
|---|---|---|---|---|
| First Region 72 | 1100 | 0 | 0 | 0 |
| Second Region 74 | 733 | 380 | 0 | 0 |
| Third Region 76 | 367 | 760 | 0 | 0 |
| Fourth Region 78 | 0 | 1026 | 114 | 0 |
| Fifth Region 80 | 0 | 1140 | 0 | 0 |
| Sixth Region 82 | 0 | 977 | 0 | 163 |

The pure PBMA in first region 72 can act as a primer and afford good adhesion with the stent surface. Also, one disadvantage of the current coating processes is that there is poor interlayer compatibility among some components, such as polymeric materials. Certain polymeric materials, for instance, do not properly adhere to each other when they are applied in layers in their pure form. The graduated interface between the PBMA and EVAL in regions 72, 74 and 76, as depicted numerically in Table II, may provide better interlayer adhesion.

In a further embodiment of the present invention, the coating formulation includes ingredient U, ingredient V, ingredient W and ingredient X. In one exemplary implementation of the ingredients of Table III, ingredient U is PBMA, ingredient V is EVAL, ingredient W is β-Estradiol, and ingredient X is the benzylalkonium salt of heparin (BAK Heparin).

TABLE III

Concentration (mg/ml)

| Region | Ingredient U | Ingredient V | Ingredient W | Ingredient X |
|---|---|---|---|---|
| First Region 72 | 0 | 1140 | 0 | 0 |
| Second Region 74 | 0 | 760 | 380 | 0 |
| Third Region 76 | 550 | 570 | 0 | 0 |
| Fourth Region 78 | 1100 | 0 | 0 | 0 |
| Fifth Region 80 | 550 | 570 | 0 | 0 |
| Sixth Region 82 | 0 | 1026 | 0 | 114 |

Composition of Coating Formulation

The ingredients contained in the coating formulation can be prepared by conventional methods. More particularly, in accordance to one embodiment, a predetermined amount of a polymeric material or combination of polymeric materials can be added to a predetermined amount of a solvent or a combination of solvents. If necessary, heating, stirring and/or mixing can be employed to effect dissolution of the polymeric material(s) into the solvent(s) for example in an 80° C. water bath for two hours.

A therapeutic substance can be also be an ingredient contained in the coating formulation. In accordance to one embodiment, a predetermined amount of a therapeutic substance or combination of therapeutic substances can be added to a predetermined amount of a solvent, a combination of solvents, with or without a polymeric material. The therapeutic substance should be in true solution or saturated in the composition of the coating formulation. If the therapeutic substance is not completely soluble in the composition, operations including mixing, stirring, and/or agitation can be employed to effect homogeneity of the residues. The therapeutic substance may be added so that dispersion is in fine particles. The mixing of the therapeutic substance can be conducted at ambient pressure and at room temperature.

Representative examples of polymeric material that can be used to coat a medical device in accordance with the present invention include ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly (ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; and carboxymethyl cellulose. EVAL is functionally a very suitable choice of polymeric material. The copolymer possesses good adhesive qualities to the surface of a stent, particularly stainless steel surfaces, and has illustrated the ability to expand with a stent without any significant detachment of the copolymer from the surface of the stent. The copolymer, moreover, allows for good control capabilities over the release rate of the therapeutic substance.

Representative examples of solvents include chloroform, acetone, water (buffered saline), dimethylsulfoxide (DMSO), propylene glycol methyl ether (PM,) iso-propylalcohol (IPA), n-propylalcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachlroro ethylene, tetrachloro ethane, chlorobenzene, 1,1,1-trichloroethane, formamide, pentane, trifluoroethanol, hexafluoroisopropanol, freon, hexamethylphosphorustriamide, and combinations thereof.

The therapeutic substance can be for inhibiting the activity of vascular smooth muscle cells. More specifically, the therapeutic substance can be aimed at inhibiting abnormal or inappropriate migration and/or proliferation of smooth muscle cells for the inhibition of restenosis. The therapeutic substance can also include any substance capable of exerting a therapeutic or prophylactic effect in the practice of the present invention. For example, the therapeutic substance can be for enhancing wound healing in a vascular site or improving the structural and elastic properties of the vascular site. Examples of therapeutic substances include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiailergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack, N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin and dexamethasone. Other therapeutic substances or agents which may be appropriate include alpha-interferon, genetically engineered epithelial cells, rapamycin and dexamethasone. The foregoing substances are listed by way of example and are not meant to be limiting. Other therapeutic substances which are currently available or that may be developed in the future are equally applicable.

The dosage or concentration of the therapeutic substance required to produce a favorable therapeutic effect should be less than the level at which the therapeutic substance produces toxic effects and greater than the level at which non-therapeutic results are obtained. The dosage or concentration of the therapeutic substance required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

While particular embodiments of the present invention have been shown and described, it will be obvious to those skilled in the art that changes and modifications can be made without departing from the embodiments this invention in its broader aspects and, therefore, the appended claims are to encompass within their scope all such changes and modifications as fall within the true spirit and scope of the embodiments this invention.

What is claimed is:

1. A method of coating an implantable medical device, comprising:
    applying a first composition onto an implantable medical device, the first composition including a first substance, a second substance and at least one solvent; and
    applying a second composition onto the device before all of the solvent has been removed from the first composition on the device, the second composition having a different relative concentration of the first substance to the second substance as compared to the first composition.

2. The method of claim 1, wherein the device is a stent.

3. The method of claim 1, wherein the first and second substances are different polymeric materials.

4. The method of claim 1, wherein the first and second substances are different therapeutic substances.

5. The method of claim 1, wherein the first substance is a polymeric material and the second substance is a therapeutic substance.

* * * * *